US00PP14195P39

(12) United States Plant Patent
Turner

(10) Patent No.: US PP14,195 P3
(45) Date of Patent: Sep. 30, 2003

(54) BRACTEANTHA PLANT NAMED 'CREAM'

(50) Latin Name: *Bracteantha bracteata*
Varietal Denomination: 'Cream'

(75) Inventor: Matthew Turner, Penrith South (AU)

(73) Assignee: Oasis Horticultural PTY, Ltd. (AU)

( * ) Notice: Subject to any disclaimer, the term of this patent is extended or adjusted under 35 U.S.C. 154(b) by 0 days.

(21) Appl. No.: 09/819,340

(22) Filed: Mar. 28, 2001

(65) Prior Publication Data

US 2002/0174473 P1 Nov. 21, 2002

(51) Int. Cl.[7] ..... A01H 5/00

(52) U.S. Cl. ..... Plt./359

(58) Field of Search ..... Plt./359

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct Bracteantha plant named Cream, characterized by its cream colored flowers, upright mounded habit, and medium green leaves.

1 Drawing Sheet

Latine name of the genus and species of the plant claimed: *Bracteantha bracteata.*
Variety denomination: 'Cream'.

BACKGROUND OF THE INVENTION

The present invention comprises a new and distinct Bracteantha plant, botanically known as *Bracteantha bracteata* and hereinafter referred to by the cultivar name 'Cream'.

The new cultivar was developed by the inventor through a controlled breeding program at New South Wales, Australia.

The female (seed) parent of 'Cream' was cultivar 'Diamond Head' (not patented in the United States). The female (seed) parent is characterized by its yellow (RHS 9A) bract color. The male (pollen) parent of 'Cream' was the proprietary selection designated 'C-1' (not patented in the United States). The male parent is characterized by its tall height and yellow (RHS 1D) bract color. 'Cream' was selected as one of the flowering progeny of the above cross.

Asexual reproduction of the new cultivar by terminal tip cuttings has demonstrated that the characteristics of the new cultivar as herein described are firmly fixed and retained through successive generations of such asexual propagation. The new cultivar was asexually reproduced in Arroyo Grande, Calif. and West Chicago, Ill.

SUMMARY OF THE INVENTION

It was found that the cultivar of the present invention (a) exhibits cream colored flowers, (b) forms medium green foliage, (c) exhibits a good basal branching character, and (d) exhibits an upright growth habit.

When the new cultivar of the present invention is compared to 'Florabella White', it is found that the new cultivar is more compact, has shorter internodes, different stem and leaf texture and darker flower color as detailed below, in Table 1.

TABLE 1

| CHARACTERISTIC | CREAM | FLORABELLA WHITE |
|---|---|---|
| PLANT HEIGHT-CM | 15 | 24 |
| PLANT DIAMETER-CM | 30 | 20 |
| # LATERAL BRANCHES | 13 | 11 |
| INTERNODE LENGTH-CM | .5 | 1.5 |
| STEM TEXTURE | HIRSUTE | TOMENTOSE |
| STEM COLOR | 145A | 144B |
| LEAF TEXTURE | PUBERULENT | SMOOTH |
| PEDUNCLE TEXTURE | PUBERULENT | TOMENTOSE |
| RAY FLORET COLOR-UPPER AND LOWER SURFACE | 4C WITH 4A AT TIP | 155A |

BRIEF DESCRIPTION OF THE PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill., USA.

DETAILED BOTANICAL DESCRIPTION

The 'Cream' cultivar has not been observed under all possible environmental conditions to date. Accordingly, it is possible that the phenotype may vary somewhat with variations in the environment, such as temperature, light intensity, and day length.

The chart used in the identification of colors described herein is the R.H.S. Colour Chart of The Royal Horticultural Society, London, England. The color values were determined on Feb. 15, 2001. The readings were taken between 10:00 and 11:00 a.m. under natural daylight conditions. The plants were produced from cuttings taken from stock plants and grown in a double polycarbonate covered greenhouse under conditions comparable to those used in commercial practice while utilizing a soilless growth medium and maintaining temperatures of approximately 72° F. during the day and approximately 65° F. during the night. Plants used for the following descriptions and measurements were grown for 14 weeks after the planting of rooted cuttings.

Classification:

*Botanical.*—*Bracteantha bracteata* cultivar Cream.

*Commercial.*—Helichrysum.

Parentage:

*Female parent.*—'Diamond Head'.

*Male parent.*—Proprietary selection designated 'C-1'.

Propagation:

*Type cutting.*—Terminal tip.

*Time to initiate roots.*—Approximately 30 to 50 days with the shorter times generally being experienced in the summer and the longer times in the winter.

Plant description:

*Habit of growth.*—Moderately vigorous with good basal branching. Pinching improved basal branching. A mature plant, 14 weeks after the planting of a rooted cutting, commonly measures approximately 15 cm in height, approximately 30 cm in diameter.

*Form.*—Upright, mounded.

*Lateral stem.*—Diameter: Approximately 4 mm. Texture: Hirsute. Color: 145B. Internode length: Approximately 4 mm.

*Foliage.*—Arrangement: Alternate. Shape: Lanceolate with entire margin, broadly acute apex and clasping base. Size: Approximately 8.8 cm in length and approximately 9 mm at widest point. Upper surface is rough and 137A. Lower surface is smooth and 137C. Venation is 145C.

Flowering description:

*Flowering habit.*—Freely flowering.

*Natural flowering season.*—Spring through fall.

*Inflorescence type.*—Single, composite, persistent.

*Bud.*—Size: 2 cm in length, 2 cm in diameter. Flower bud color, just before opening is 11C.

*Inflorescence diameter.*—Approximately 4.2 cm.

*Involucral bracts.*—Quantity: Approximately 13 whorls. Appearance: Smooth, papery. Shape: Linear. Length: 1.2 cm. Width: From 1 to 4 mm.

*Capitulum.*—Diameter is approximately 16 cm, depth is approximately 13 mm.

*Disc florets.*—Shape: Tubular. Length: Approximately 9 mm. Color of immature disk florets is 21C. Color of mature disc florets is 21A.

*Flower color.*—Upper and lower surface, fully opened involucral bract: 4C with 4A at tip.

*Peduncle.*—Length: Approximately 8 cm. Color: 146C. Texture: Puberulent. Strength: Strong.

*Fragrance.*—None.

*Reproductive organs.*—Stigma color 21A. Style: One per disc floret. Length: Approximately 2 mm. Color: 3C. Anthers: Two per disc floret, 2 mm in length, and 16A in color. Pollen color: 15A.

*Lastingness of the flowers.*—The lastingness of fresh cut flowers of the new cultivar is not known as they are not used as fresh cut flowers. They would be expected to last indefinitely as dried flowers but may fall apart after six to twelve months.

Seed development: Seed production has not been observed.

Disease resistance: Resistance to pathogens common to Bracteantha has not been observed.

I claim:

1. A new and distinct cultivar of Bracteantha plant named 'Cream' substantially as herein shown and described, which:

(a) exhibits cream colored flowers, (b) forms medium green foliage, (c) exhibits a good basal branching character, and (d) exhibits an upright mounded and trailing growth habit.

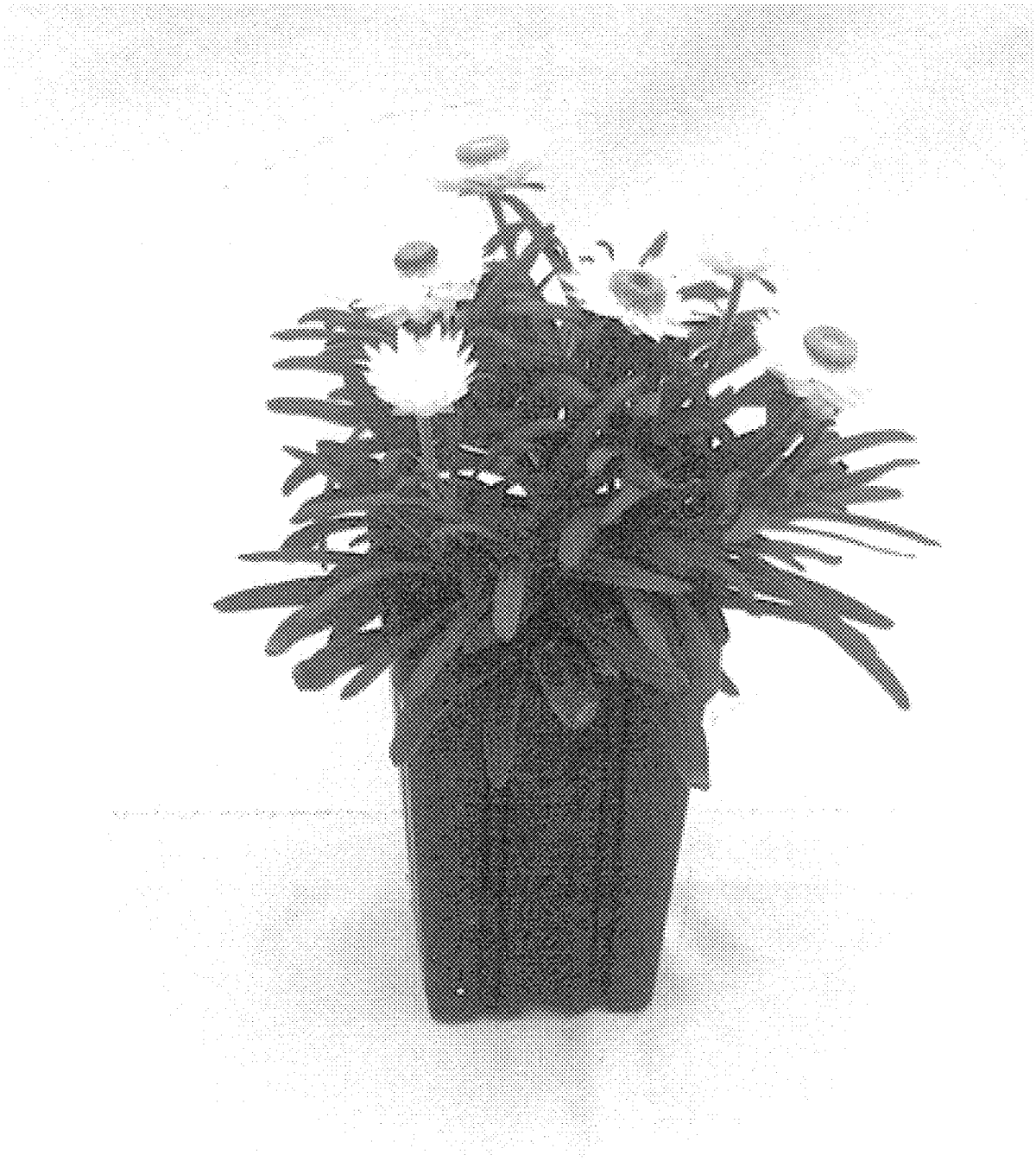

* * * * *